United States Patent
Bell et al.

(10) Patent No.: US 8,697,405 B2
(45) Date of Patent: *Apr. 15, 2014

(54) PROCESS FOR THE PRODUCTION OF ETHANOL AND BUTANOL

(75) Inventors: Peter Simpson Bell, Dunblane (GB); Stephen John Benstead, Callander (GB); Neil Turnbull, Fife (GB)

(73) Assignee: Ineos USA LLC, Lisle, IL (US)

( * ) Notice: Subject to any disclaimer, the term of this patent is extended or adjusted under 35 U.S.C. 154(b) by 279 days.

This patent is subject to a terminal disclaimer.

(21) Appl. No.: 12/736,102

(22) PCT Filed: Feb. 19, 2009

(86) PCT No.: PCT/EP2009/051963
§ 371 (c)(1),
(2), (4) Date: Sep. 9, 2010

(87) PCT Pub. No.: WO2009/112334
PCT Pub. Date: Sep. 17, 2009

(65) Prior Publication Data
US 2010/0330640 A1    Dec. 30, 2010

(30) Foreign Application Priority Data

Mar. 11, 2008 (EP) ................................ 08102478
May 19, 2008 (EP) ................................ 08156460

(51) Int. Cl.
| C12P 7/06 | (2006.01) |
| C12P 39/00 | (2006.01) |
| C12P 7/54 | (2006.01) |
| C12P 7/52 | (2006.01) |
| C12P 7/14 | (2006.01) |
| C12P 7/08 | (2006.01) |

(52) U.S. Cl.
USPC ............. 435/161; 435/42; 435/140; 435/141; 435/162; 435/163; 435/819; 435/842

(58) Field of Classification Search
USPC .......................................... 435/161, 136, 160
See application file for complete search history.

(56) References Cited

U.S. PATENT DOCUMENTS

| 4,935,360 A * | 6/1990 | Klemps et al. ................. 435/140 |
| 5,753,474 A | 5/1998 | Ramney |
| 5,842,357 A * | 12/1998 | Siwajek et al. ................. 62/625 |
| 6,043,392 A * | 3/2000 | Holtzapple et al. ........... 562/513 |
| 6,136,577 A | 10/2000 | Gaddy |
| 7,285,402 B2 * | 10/2007 | Gaddy et al. .................. 435/161 |
| 2003/0211585 A1 | 11/2003 | Gaddy |
| 2007/0117195 A1 * | 5/2007 | Warner et al. ................. 435/161 |
| 2007/0275447 A1 * | 11/2007 | Lewis et al. ................... 435/161 |

FOREIGN PATENT DOCUMENTS

| EP | 2 257 633 | 8/2010 |
| WO | WO 00/53791 | 9/2000 |
| WO | WO 2006/119052 | 11/2006 |
| WO | WO 2008/115080 | 9/2008 |
| WO | WO 2009/112335 | 9/2009 |

OTHER PUBLICATIONS

Meyer, C.L., "Carbon Monoxide Gasing Leads to Alcohol Production and Butyrate Uptake Without Acetone Formation in Continuous Cultures of *Clostridium-acetobutylicum*", Applied Microbiology and Biotechnology, vol. 24, No. 2, 1986, pp. 159-167, XP008024862; ISSN: 0175-7598 abstract.

Meyer, C.L., "The Effect of CO on Growth and Product Formation in Batch Cultures of *Clostridium acetobutylicum*", Biotechnology Letters, vol. 7, No. 1, 1985, pp. 37-42.

* cited by examiner

*Primary Examiner* — Taeyoon Kim
*Assistant Examiner* — Srikanth Patury
(74) *Attorney, Agent, or Firm* — Vikrant B. Panchal; Ineos USA LLC

(57) ABSTRACT

The present invention relates to a process for the production of ethanol comprising both gasification and fermentation of feedstocks, and, in particular to a process for the production of ethanol comprising: a) passing a biomass feedstock to a first fermentation step wherein it is subjected to anaerobic fermentation at a pH below 6.0 and at a temperature in the range 20 to 700C to convert the biomass to a solution comprising acetic acid as the predominant product, b) passing a gasifiable feedstock to a gasification step wherein it is subjected to gasification to produce a gaseous mixture comprising carbon monoxide and hydrogen, and c) passing the solution comprising acetic acid from step (a) and the gaseous mixture from step (b) to one or more further fermentation steps wherein they are subject to fermentation to produce ethanol.

7 Claims, No Drawings

PROCESS FOR THE PRODUCTION OF ETHANOL AND BUTANOL

The present invention relates to a process for the production of ethanol comprising both gasification and fermentation of suitable feedstocks.

It has been known for many years that bacteria cause the anaerobic fermentation or digestion of biomass resulting in various gases which can be utilised. As early as the late 19$^{th}$ Century the products of anaerobic digestion were used to generate methane gas for use in street lighting. More recently, anaerobic fermentation has been considered as both a means to reduce the amount of organic matter which is sent to landfill and as an alternative method for production of useful chemicals, such as alcohols.

For example, U.S. Pat. No. 5,753,474 describes a continuous two-stage anaerobic fermentation process to produce butanol using two different strains of bacteria.

There are also known anaerobic fermentation processes for the production of alcohols from biomass feedstocks via gasification of the feedstock to produce carbon monoxide and hydrogen, followed by fermentation into C2+alcohols using anaerobic bacteria. Examples of suitable carbon monoxide fermentation processes can be found, for example, in US 2003/0211585 and US 2007/0275447, and are also described in DOE reports under DOE Contract Number DE-AC22-92PC92118, such as "Bench-scale Demonstration of Biological Production of Ethanol from Coal Synthesis Gas", Topical Report 5, November 1995.

A number of bacteria are known which can produce ethanol from the carbon oxides and hydrogen in such a process, and the selectivity to ethanol may be controlled both by selection of bacteria and by control of the reaction conditions, generally to keep the bacteria functioning and to favour ethanol production over competing products, such as acetic acid. Specific examples of bacteria and processes can be found in US 2003/0211585 and US 2007/0275447.

It has now been found that ethanol may be advantageously produced from biomass feedstocks via a process in which both a gasification step and a first fermentation step are applied to the initial biomass, with at least one further fermentation step applied to the products from the gasification and first fermentation step to produce ethanol.

Thus, in a first aspect, the present invention provides a process for the production of ethanol, said process comprising:
a) passing a biomass feedstock to a first fermentation step wherein it is subjected to anaerobic fermentation at a pH below 6.0 and at a temperature in the range 20 to 70° C. to convert the biomass to a solution comprising acetic acid as the predominant product,
b) passing a gasifiable feedstock to a gasification step wherein it is subjected to gasification to produce a gaseous mixture comprising carbon monoxide and hydrogen, and
c) passing the solution comprising acetic acid from step (a) and the gaseous mixture from step (b) to one or more further fermentation steps wherein they are subject to fermentation to produce ethanol.

The present invention provides a number of advantages over the known processes for the production of ethanol from biomass via gasification, especially as described in U.S. 2003/0211585 and US 2007/0275447.

In particular, processes for production of ethanol from biomass via gasification, such as described in US 2003/0211585, tend to be net $CO_2$ producers. This $CO_2$ production may actually arise from either step of the process. Thus, the gasification step itself generally produces $CO_2$ as well as CO and $H_2$. However, in addition, although fermentation routes to higher alcohols (ethanol and heavier alcohols) from carbon monoxide may, in theory, utilise $CO_2$ as a reactant for the production of the higher alcohols, in practise the fermentation reaction also tends to be a net producer of carbon dioxide.

In particular, the bacteria used for fermentation can produce alcohols according to either of the following 2 reactions:

$$6CO + 3H_2O \rightarrow C_2H_5OH + 4CO_2 \qquad (1)$$

$$2CO_2 + 6H_2 \rightarrow C_2H_5OH + 3H_2O \qquad (2)$$

However, the CO conversion is typically 70-90% per pass while the $H_2$ conversion is typically less than the CO conversion—therefore fermentation is also a net producer of $CO_2$, the overall gasification and syngas fermentation process tending to produce several moles of $CO_2$ for every mole of ethanol produced.

In contrast, fermentation of biomass feedstock under conditions to convert the biomass (or at least the fermentable portion thereof) to a product comprising acetic acid (the first fermentation step of the present invention), which is then converted to ethanol is a much more efficient use of the carbon content of the biomass feedstock than gasification.

In a "conventional" fermentation process via acetic acid the net reaction which occurs can be considered as:

$$C_6H_{12}O_6 ==> 2C_2H_5OH + 2CO_2. \qquad (3)$$

Whilst this reaction also generates $CO_2$, the amount produced is only one $CO_2$ for every ethanol.

It is therefore advantageous to pass as much fermentable biomass as possible to such a process rather than to gasification, since this results in a reduction of carbon dioxide produced.

The gasification step in the process of the present invention is still important however since many feedstocks (or components of potential feedstocks) cannot be fermented, but are gasifiable. Examples of such feedstocks are non-biomass feedstocks, such as plastics, and non-biodegradable biomass feedstocks, such as lignins.

Preferably, the biomass feedstock passed to the first fermentation step and the gasifiable feedstock passed to a gasification step derive from a single mixed waste feed comprising both fermentable and gasifiable components.

In particular, the use of both a first fermentation step and a gasification step in the process of the present invention is particularly advantageous in that it is possible to utilise efficiently a mixed waste feed comprising both fermentable and gasifiable (but non-fermentable) components, whilst minimising environmental impact compared to use of gasification of such feedstocks alone. Taking a general example, a mixed waste feed, after separation to remove recyclable materials such as glass, may be treated to separate a first feedstock comprising fermentable components for use as the biomass feedstock for the first fermentation step of the present invention, and a second feedstock comprising gasifiable components for use as the gasifiable feedstock for the gasification step of the present invention.

Alternatively, or additionally, the gasifiable feedstock for the gasification step of the present invention may comprise residual components, for example non-fermentable components, from the first fermentation step i.e. a biomass feedstock may be subjected to the first fermentation step to produce a solution comprising acetic acid and a solid residual which solids are passed as the gasifiable feedstock for the gasification step of the present invention.

Thus, compared to the processes of US 2003/0211585 and US 2007/0275447 the present invention utilises a first fermentation step to produce a product comprising acetic acid, reducing the carbon dioxide footprint of a process using just a gasifier with fermentation of the carbon monoxide and hydrogen produced on the initial feedstock.

The biomass feedstock in step (a) may be any suitable biomass feedstock including, but not limited to, municipal solid waste, lignocellulosic biomass, landfill leachate, carbohydrates, fats and proteins. Specific examples are the biodegradable portion of municipal and industrial wastes, biosludge, energy crops and agricultural residues.

The feedstock may be treated by conventional means, such as milling, to make it more easily digested during fermentation. Advantageously, the feedstock is not pasteurised or sterilised to remove bacteria therefrom, such a process not being necessary in the present invention.

As used herein, "sterilise" means to treat to effectively kill all bacteria therein. This is typically achieved by application of heat, although other means, such as irradiation, are also known.

As used herein, "pasteurise" means to treat for the purpose of killing bacteria to achieve a 5-log reduction (0.00001 times the original) in the number of live bacteria. Thus, pasteurisation can be distinguished from sterilisation in that some bacteria survive the process. Pasteurisation is typically also performed by the application of heat, generally at lower temperature and/or for a shorter period of time than a corresponding sterilisation. Again, other means, such as irradiation, are also known.

The feedstock pre-treatment is generally selected dependent on the specific feedstock and as necessary or advantageous to make the feedstock more suitable for fermentation. Typically this involves methods to effect size reduction in order to provide improved access for the bacteria and improve the rate of conversion. Examples of known techniques are shredding, milling, ultrasound, hydrocrushing, steam explosion.

The treatment may also include treatment to remove or reduce gasifiable but non-fermentable components which can then be passed to the gasification step of the present invention.

The biomass feedstock is subjected to anaerobic fermentation under conditions to convert (ferment) biomass to a solution comprising acetic acid.

A single bacterial strain may be used, but generally the most effective processes use a mixture of bacterial strains. A particular advantage of the use of a mixture of bacterial strains is that the first fermentation step can be applied widely to different types of biomass because of the mixture of bacterial strains present. In the present invention, the mixture of bacterial strains may include bacterial strains present in the biomass feedstock. As noted above, therefore, the feedstock need not be pasteurised or sterilised to remove bacteria therefrom.

There are four key stages in normal anaerobic digestion: hydrolysis, acidogenesis, acetogenesis and methanogenesis. Through hydrolysis, complex organic molecules are broken down into simple sugars, acids and amino acids. Bacteria convert these molecules to volatile fatty acids through the process of acidogenesis. In the third stage, acetogenesis of the volatile fatty acids occurs and they are converted to carboxylic acids, such as acetic acid and butyric acid. The final stage in normal anaerobic digestion is methanogenesis, in which acetic acid is broken down to form methane and carbon dioxide.

Generally, the bacteria present in anaerobic digestion can be classified by the final product as either acetogens or methanogens. Both types are likely to be present in step (a) of the present invention.

In general, in a fermentation process in which a mixture of bacterial strains are present, certain bacteria will "thrive", whilst others will not. The bacteria which will thrive will be those that can grow under the conditions of the fermentation. Other bacteria may survive (but be "inhibited") or may die. In any such fermentation it may be difficult to determine the exact mixture of bacterial strains present, and populations of certain bacteria may vary significantly with what may otherwise seem minor changes in fermentation conditions. Nevertheless, by selection of conditions which have been found to favour the production of the desired product(s), bacteria which produce such product(s) will be selectively maintained in the reactor. The use of a mixture of bacterial strains present in the first fermentation step will also enable the bacterial populations to adjust (or "evolve") when the feedstock is changed to favour those which thrive on the particular feedstock. Processes in which mixtures of bacteria are utilised to produce particularly desired products are described, for example, in US 2003/211585 and US 2006/024801.

In the process of the present invention, the conditions in the first fermentation step are maintained to favour a product comprising acetic acid as the predominant product, which effectively means conditions that inhibit any methanogenic bacteria, but which allow acetogenic bacteria to thrive. The principal condition necessary for this is the pH, and in the process of the present invention the pH is maintained below 6.0, preferably at a pH in the range 3 to 5.5. At this pH the methanogenic bacteria are inhibited in their activity and reproduction. Generally, acetogenic bacteria also prefer higher temperatures than methanogenic bacteria. Therefore, whilst temperatures in the range 20 to 70° C. may be utilised, preferably the temperature in the first fermentation step is in the range 40 to 60° C., which further inhibits the methanogenic bacteria and favours the acetogenic bacteria.

Under such conditions, acid production is favoured whilst production of methane is inhibited. "Wash out" of the methanogens from the bacterial mass can also occur (the draining of methanogenic bacteria through the outlet of the reactor/digester at a faster rate than their generation). Although "higher" acids such as propionic and butyric acids are also produced by digestion of the biomass, these can be further broken down to acetic acid. In contrast, acetic acid is not broken down further e.g. to formic acid and thus, although butyric acid and other "higher" acids are obtained in the present invention they are generally obtained in smaller amounts than the acetic acid. In the process of the present invention, the acetic acid is the predominant product from step (a), by which is meant that acetic acid is present in higher concentration than any other products. The product distribution in the product stream may be controlled by the conditions in the first fermentation step. Preferably the acetic acid is present in a concentration of at least 60 wt %, preferably at least 80 wt % of the total weight of carboxylic acids in the product stream. The second most predominant product is usually butyric acid. Usually the product stream comprises at least a 2:1 weight ratio of acetic acid to butyric acid.

It should be noted that the acetic acid, butyric acid and other "acids" produced may not actually all be present in the fermentation broth solely in the form of the acid, but, for example, may be present as acetate or other related compounds, which are only formally converted to acetic acid if suitably "worked-up" from the fermentation broth. Nevertheless, it is customary in the art of fermentation to use the term "acids" to refer to all such compounds, and the yields thereof, even if they are not in the free acid form in the fermentation broth. For avoidance of any doubt, as used herein, general reference to acetic acid, butyric acid or other acids in a fermentation broth includes salts, complexed and chelated compounds thereof, as well as the free acids themselves.

It has also been found that temperature can be used to control the relative amounts of various acids formed in step (a). In particular, temperatures in the range of 50 to 60° C. significantly increase the production of acetic acid over butyric acid and other "higher" acids even compared to lower temperatures in the preferred range of 40 to 60° C., and are thus even more preferred. Under such conditions, the product stream may comprise at least a 4:1 weight ratio of acetic acid to butyric acid and a concentration of the acetic acid of at least 90 wt % of the total weight of carboxylic acids in the product stream.

Nutrients may be added to the first fermentation step as and if required. For example, whilst most manures and complex feedstocks usually inherently contain sufficient nutrients for the bacteria in step (a), other feedstocks, such as industrial wastes and crop residues may be deficient. Typical nutrients requirements include nitrogen, phosphorous, magnesium, sodium, manganese, calcium and cobalt. Nutrients are preferably added by mixture of nutrient rich feedstocks, such as manure, with those that may be nutrient-deficient.

An example of a suitable fermentation process for step (a) is bulk fermentation of a biomass pile as described in US 2006/0024801, but any suitable fermentation tank or vessel may also be used. A number of fermentation tanks/vessels are commercially available, such as the Induced Blanket Reactor available from Andigen LC of Ohio, USA.

Step (a) produces an initial product solution comprising acetic acid, bacteria and residual solids which can be removed from the first fermentation step. Typically, this product solution is separated from any residual solids to produce a solution comprising the acetic acid suitable for use in step (c).

A suitable means of separation for any residual solids is filtration. In one embodiment, the separated residual solids may be passed as all or part of the gasifiable feedstock in step (b).

Optionally, bacteria from the first fermentation step are also separated. For example, bacteria may be separated by filtration with a suitably small mesh filter. Alternatively, or in addition to a filtration to remove bacteria, the solution may be pasteurised or sterilised.

The product stream from step (a) is removed in the form of a dilute solution in water. The solution preferably has a concentration of acetic acid in solution of 1 to 5 wt %, more typically 2 to 5 wt %. The concentration of products in said stream can be controlled by the rate at which the product stream is removed from the fermentation.

At higher concentrations of acetic acid, the acetic acid may inhibit formation of further acid, even to the extent that the acids can kill the bacteria. Although the solution removed from step (a) is relatively dilute, no concentration is required before the subsequent fermentation to produce ethanol therefrom.

In step (b) of the process of the present invention a gasifiable feedstock is passed to a gasification step and subjected to a gasification to produce a gaseous mixture comprising carbon monoxide and hydrogen.

The gasifiable feedstock may be any suitable gasifiable feedstock. As already described, the preferred gasifiable feedstock comprises waste plastics and/or non-fermentable components of a mixed waste feed, the fermentable components of which are passed to the first fermentation step as the biomass feedstock in step (a).

There may also be fed to the gasification step of step (b) co-feeds, such as methane or coal. Methane, for example, can be fed to the gasification step to increase the $H_2$:CO ratio obtained from the gasification.

As one example, although the first fermentation step is operated to favour acid formation and inhibit methane formation, if any methane is formed in the first fermentation step this may be cycled to the gasification step.

In a particularly preferred embodiment, the process of the present invention is applied to a mixed waste feed obtained from or at a landfill site. Such a site produces what is termed "landfill gas" which is a mixture of predominantly methane, carbon dioxide and hydrogen sulphide, and which must normally be reformed or combusted in an on-site facility. In the process of the present invention, this landfill gas may be passed as a co-feed to the gasification step (b) along with the non-fermentable components of the landfill derived mixed waste feed (gasifiable feedstock).

The landfill gas may be passed to the gasification step without treatment.

This can not only avoid the need for separate treatment of the landfill gas, but also will result in an increased hydrogen generation in the gasification step. An increase in hydrogen generally favours ethanol production over acetic acid in the subsequent fermentation of carbon monoxide and hydrogen to ethanol.

Any suitable gasification process may be used in the gasification step. A large number of gasification processes are known to the person skilled in the art. For example, representative examples of suitable processes include those described in WO 2007/143673, WO 2007/131241 and U.S. Pat. No. 6,817,388.

In step (c) of the process of the present invention the solution comprising acetic acid from step (a) and the gaseous mixture from step (b) are passed to one or more further fermentation steps wherein they are subject to fermentation to produce ethanol.

In one embodiment, the solution comprising acetic acid from step (a) and the gaseous mixture from step (b) are passed to separate fermentation steps. Thus, the solution comprising acetic acid from step (a) may be passed to a fermentation step wherein it is contacted with a bacteria capable of converting acetic acid to ethanol, whilst the gaseous mixture from step (b) is passed to a fermentation step for the production of ethanol from carbon monoxide and hydrogen utilising an anaerobic acetogenic bacteria. The conversion of carboxylic acids to their corresponding alcohols, known as solventogenesis is described, for example, in U.S. Pat. No. 5,853,474. A number of bacteria, hereinafter defined as solventogenic bacteria, which are capable of converting carboxylic acids to their corresponding alcohols are known and any such solventogenic bacteria may be used. Examples of suitable solventogenic bacteria which may be used include *Acetogenium kivui, Acetobacterium woodii, Acetoanaerobium noterae, Clostridium aceticum, Butyribacterium methylotrophicum, Clostridium acetobutylicum, Clostridium thermoaceticum, Eubacterium limosum, Clostridium ljungdahlii, Peptostreptococcus productus, Clostridium carboxydivorans, Clostridium beijerinkii, Clostridium aurantibutyricum,* and *Clostridium tetanomorphum*. Particularly suitable examples are *Clostridium ljungdahlii, Clostridium carboxydivorans, Clostridium acetobutylicum, Clostridium beijerinkii, Clostridium aurantibutyricum,* and *Clostridium tetanomor-*

*phum. Clostridium ljungdahlii, Clostridium carboxydivorans* and *Clostridium acetobutylicum* are most preferred.

The conversion of gaseous mixtures comprising carbon monoxide and hydrogen to produce ethanol utilising an anaerobic acetogenic bacteria is also known and is described, for example, in the aforementioned US 2003/0211585 and US 2007/0275447. The conditions in the fermentation step are selected to favour ethanol production over acetic acid, as described in US 2003/0211585.

The anaerobic acetogenic bacteria for this step are not especially limited as long as they are able to convert CO and H2 into ethanol. Useful bacteria include, without limitation, those described in US 2003/0211585 and US 2007/0275447, namely *Acetogenium kivui, Acetobacterium woodii, Acetoanaerobium noterae, Clostridium aceticum, Butyribacterium methylotrophicum, Clostridium acetobutylicum, Clostridium thermoaceticum, Eubacterium limosum, Clostridium ljungdahlii* (especially strains *Clostridium ljungdahlii* PETC, *Clostridium ljungdahlii* ERI2, *Clostridium ljungdahlii* C-01 and *Clostridium ljungdahlii* O-52), *Peptostreptococcus productus* and *Clostridium carboxydivorans* (especially strains P7 and P11).

Particularly preferred bacteria are *Clostridium ljungdahlii* and *Clostridium carboxydivorans*.

The process of this embodiment of the first aspect of the present invention results in separate product streams comprising ethanol. Preferably said ethanol product streams are combined and passed to a common ethanol treatment/separations section, avoiding unnecessary duplication of equipment.

It may be noted that the anaerobic acetogenic bacteria which are suitable for the conversion of gaseous mixtures comprising carbon monoxide and hydrogen to produce ethanol are also bacteria which have been previously listed as solventogenic bacteria, which are capable of converting carboxylic acids to their corresponding alcohols.

Thus, in a second, and most preferred, embodiment of the present invention both the solution comprising acetic acid from step (a) and the gaseous mixture comprising carbon monoxide and hydrogen from step (b) are passed to a common (second) fermentation step in step (c).

Thus, in this second embodiment, the present invention provides a process for the production of ethanol, said process comprising:
a) passing a biomass feedstock to a first fermentation step wherein it is subjected to anaerobic fermentation under conditions to convert the biomass to a solution comprising acetic acid,
b) passing a gasifiable feedstock to a gasification step wherein it is subjected to gasification to produce a gaseous mixture comprising carbon monoxide and hydrogen, and
c) passing both the solution comprising acetic acid from step (a) and the gaseous mixture from step (b) to a second fermentation step wherein they are subject to fermentation in the presence of an anaerobic acetogenic bacteria to produce ethanol.

An obvious advantage of this embodiment is that only one further fermentation step is required in the process, rather than two. Further, however, not only can the anaerobic acetogenic bacteria suitable for ethanol production from carbon monoxide and hydrogen tolerate the acetic acid, but this embodiment actually results in a yet further increase in ethanol selectivity per unit of feedstock converted. In particular, it is known that the anaerobic acetogenic bacteria suitable for ethanol production from carbon monoxide and hydrogen, although highly selective for ethanol, generally also produce competing products, such as acetic acid, the production of which it is generally desired to minimise. US 2003/0211585, for example, seeks to control the conditions in the fermentation process to favour ethanol production over acetic acid, and in such a process any acetic acid formed is recycled to the fermentation step. In this second aspect of the present invention acetic acid is deliberately introduced into the fermentation process (second fermentation step) with the gaseous mixture comprising carbon monoxide and hydrogen to inhibit acid formation in the second fermentation step, resulting in a net acetic acid conversion, rather than any production, in this step.

Further, the $H_2$ present in the gaseous mixture from the gasification step (b) can also be utilized to convert the acetic acid from step (a) to ethanol, giving the following equations for the conversion of the fermentable components of the initial feedstock:

$$C_6H_{12}O_6 \rightarrow 3CH_3COOH \tag{4}$$

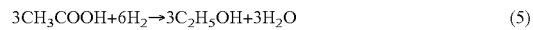
$$3CH_3COOH + 6H_2 \rightarrow 3C_2H_5OH + 3H_2O \tag{5}$$

The net reaction for this route is:

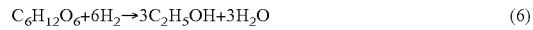
$$C_6H_{12}O_6 + 6H_2 \rightarrow 3C_2H_5OH + 3H_2O \tag{6}$$

In effect, the presence of hydrogen results in reduced $CO_2$ and increased ethanol compared to the "conventional" overall fermentation route represented by equation (3) above. Thus, compared to the first aspect of the present invention the second aspect of the present invention results in a further increased ethanol selectivity per unit of feedstock converted.

Finally, the carbon monoxide present in the feedstream to the second fermentation step is a poison to many bacteria, including those present in the first fermentation step. A further advantage of this embodiment is that separate pasteurisation or sterilisation of the bacteria in the solution from the first fermentation may be avoided, the carbon monoxide acting to sterilise the solution in-situ in the second fermentation step.

As with the first embodiment, the second fermentation step, including the preferred conditions to favour ethanol production over acetic acid are preferably as described in U.S. 2003/0211585, useful bacteria including, without limitation, those described in U.S. 2003/0211585 and US 2007/0275447, namely *Acetogenium kivui, Acetobacterium woodii, Acetoanaerobium noterae, Clostridium aceticum, Butyribacterium methylotrophicum, Clostridium acetobutylicum, Clostridium thermoaceticum, Eubacterium limosum, Clostridium ljungdahlii* (especially strains *Clostridium ljungdahlii* PETC, *Clostridium ljungdahlii* ERI2, *Clostridium ljungdahlii* C-01 and *Clostridium ljungdahlii* O-52), *Peptostreptococcus productus* and *Clostridium carboxydivorans* (especially strains P7 and P11).

Particularly preferred bacteria for step (c) for this embodiment are *Clostridium ljungdahlii* and *Clostridium carboxydivorans*.

As described in US 2003/211585, the ratio of ethanol over acetate can be increased by manipulating the bacteria in the bioreactor, in particular by reducing the redox potential or increasing the NAD(P)H to NAD(P) ratio in the fermentation broth after said bacteria achieves a stable cell concentration in said bioreactor. This manipulation can be achieved by altering at least one parameter selected from the group consisting of nutrient medium contents, nutrient feed rate, aqueous feed rate, operating pressure, operating pH, gaseous substrate contents, gas feed rate, fermentation broth agitation rate, product inhibition step, cell density, substrate inhibition and combinations thereof. Practical examples of this are, for example, supplying an excess of H2 or a slight excess of CO or limiting the amount of calcium pantothenate in solution.

The ethanol is obtained from step (c) as a dilute solution in water (or two or more dilute solutions in water where two or more further fermentation steps are used in step (c), but which are preferably combined prior to ethanol treatment/separations). Generally, the dilute ethanol product stream is treated to concentrate and separate the ethanol. The actual final purity of ethanol desired will depend on the subsequent intended use, but is typically at least 90 wt %, preferably at least 95 wt % and more preferably at least 99 wt %.

The preferred technique for treatment/purification is to use distillation. However, ethanol in water cannot be purified by simple distillation to higher than about 95 wt %, at atmospheric pressure, due to the formation of an azeotrope with water. Typically, therefore, the ethanol product is purified to about 90-95 wt % by distillation followed by a drying step, for example on molecular sieve, to give a >99 wt % product.

Other alcohols in the product stream, such as butanol, may also be removed, as required, by conventional means. Removal from the distillation column as one or more side streams is a preferred example.

The product ethanol stream from step (c) typically comprises ethanol at a concentration of ethanol in solution of 1 to 5 wt %, more typically in the range 2 to 5 wt %. Butanol is usually the next most predominant alcohol, and is typically present at a concentration of butanol in solution of up to 1 wt %, for example of 0.2 to 1 wt %, more typically in the range 0.2 to 0.75 wt %, such as 0.4 to 0.75 wt %.

In particular, when the subsequent treatment/purification comprises distillation, as described above, it is strongly preferred that the initial concentration of ethanol is in the range 2 to 5 wt %. Although such solutions are relatively dilute, it has surprisingly been found that only a small penalty in distillation duty is obtained by using initially relatively dilute feeds. In particular, it has been found that when distilling to high purity the rectification operating line is "pinched" close to the vapour-liquid equilibrium curve near to the azeotrope composition. In contrast, it has been found that the operating line at the bottom end of the vapour-liquid equilibrium curve is not pinched unless the concentration of ethanol in the initial stream is below about 2 wt %. For a higher feed concentration of ethanol the pinch remains at the same point at the top of the curve, and the rectification operating line changes minimally. This means that the reflux ratio, and hence the column duty, does not change significantly as the initial feed composition is increased.

For example, it has surprisingly been found that to produce an overheads stream having 94.5 wt % ethanol by distillation from a feed stream with 20 wt % ethanol saves only just over 10% energy compared to producing a stream of the same concentration from a feed stream with only 4 wt % ethanol.

This is in distinct contrast to what has previously been thought in the art, which was that it was not commercially viable to separate ethanol of high purity from initial streams at such low concentrations by distillation. Thus, as noted previously, in the Encyclopedia of Bioprocess Technology—Fermentation, Biocatalysis, and Bioseparation, Volumes 1-5, p.670-687 it was stated that it was not viable to separate ethanol at less than 6 to 8%.

EXAMPLE

The following example provides a comparison between the conversion of a typical municipal solid waste (MSW) using a process of gasification followed by fermentation "alone" (comparative), versus a route where 50% of the calorific value of the MSW is converted to ethanol via a first fermentation step to produce acetic acid.

On a mass basis, a typical municipal waste can be represented as:
30% cellulose/hemicellulose equivalent e.g. paper (gasifiable and digestible)
15% plastic/lignin (gasifiable but not digestible)
The remainder is composed of water, inerts and recyclables such as glass and metals (e.g. cans) (non-gasifiable and non-digestible)

On a calorific basis the 45% of gasifiable materials in the municipal waste can be represented as:
50% cellulose/hemicellulose equivalent,
17% non-digestible biomass
33% plastics Comparative Example As a comparative example the all the gasifiable materials are subject to gasification followed by fermentation of the syngas produced.

The gasification yields (by volume): 36% CO, 10% $CO_2$, 50% $H_2$ and 4% $N_2$, which translates as 42.5 kT CO, 4.2 kT of $H_2$ and 18.6 kT of $CO_2$ per 100 kT of the initial MSW feed (a typical annual processing capacity).

In the syngas fermentation, the syngas components are converted to ethanol via the following reactions:

$$6CO + 3H_2O \rightarrow C_2H_5OH + 4CO_2 \quad (1)$$

$$2CO_2 + 6H_2 \rightarrow C_2H_5OH + 3H_2O \quad (2)$$

A typical CO conversion is 80% and a typical $H_2$ conversion is 40%, which (assuming 100% selectivity to ethanol i.e. no acetic acid) produces from the fermentation of the syngas 15.7 kT of ethanol and 23.3 kT of $CO_2$. (35.6 kT of $CO_2$ is produced from the first reaction above, and 12.3 kT is consumed in the second reaction above.)

Including the $CO_2$ generated in the gasification step the overall yields of the ethanol and $CO_2$ are 15.7 kT of ethanol and 41.9 kT of $CO_2$ per 100 kT of the initial MSW feed. The amount of $CO_2$ produced compared to ethanol produced equates to 2.66 Te of CO2 per Te of ethanol.

Example 1

In comparison, to illustrate the process of the present invention the 50% by calorific value of the MSW which is digestible is instead digested to form acetic acid, which is then converted to ethanol via solventogenesis. For the purposes of this Example, the syngas from the gasification and the acetic acid from the digestion are separately converted to ethanol.

The net reaction for this route alone is:

$$C_6H_{12}O_6 \rightarrow 2C_2H_5OH + 2CO_2. \quad (3)$$

Note that the 50% by calorific value which is digestible actually equates to two thirds (30%) of the total gasifiable material by mass. Assuming an overall conversion of 100% of said portion to ethanol, this results in a net production of 15.3 kT of ethanol and 14.7 kT of $CO_2$ per 100 kT of the initial MSW.

Combined with the products from the portion of the MSW which is still passed through the gasifier, the net productions of ethanol and $CO_2$ are 23.2 kT and 35.7 kT respectively. In this Example, the amount of $CO_2$ produced compared to ethanol produced equates to 1.54 Te of CO2 per Te of ethanol.

Although the above includes some assumptions, it is quite clear that compared to gasification of the entire feed, the use digestion of a portion results in an increase of ethanol produced and a significant reduction in the $CO_2$ produced.

Example 2

To illustrate a preferred process of the present invention Example 1 is repeated except that the reactions of fermentation to ethanol of the syngas from the gasification and the solventogenesis of the acetic acid are combined in a single reactor as in the preferred second embodiment of the present invention.

In this scenario, the $H_2$ present in the syngas can be utilized to convert the acetic acid to ethanol giving the following equations for the process:

$$C_6H_{12}O_6 \rightarrow 3CH_3COOH \quad (4)$$

$$3CH_3COOH + 6H_2 \rightarrow 3C_2H_5OH + 3H_2O \quad (5)$$

(Net reaction for this route: $C_6H_{12}O_6 + 6H_2 \rightarrow 3C_2H_5OH + 3H_2O$)

In these reactions, reaction (5) utilises the hydrogen present in the syngas for conversion of the acetic acid to ethanol. For the purposes of the present comparison, this is assumed to result in a reduction in the syngas fermentation of hydrogen via equation (2) above ($2CO_2 + 6H_2 \rightarrow C_2H_5OH + 3H_2O$) because of a competition for available hydrogen, but even in this scenario will result in a further net increase in ethanol production and a further net reduction in $CO_2$ production.

For example, assuming 75% conversion of acetic acid to ethanol via equation (5) and that this replaces completely any ethanol production via equation (2), the net productions of ethanol and $CO_2$ are 21.95 kT and 27.1 kT respectively.

Although the absolute amount of ethanol produced is slightly reduced compared to Example 1 (due principally to a cautious assessment of the acetic acid to ethanol conversion via equation (5)), the net $CO_2$ production is significantly reduced further still. In this Example, the amount of $CO_2$ produced compared to ethanol produced equates to only 1.23 Te of CO2 per Te of ethanol.

Further, this assumes reaction (2) does not occur. In contrast, if reactions (2) and (5) could both occur this would result in yet a further increase in ethanol and reduction in $CO_2$ produced. This would be the case if enough hydrogen were available in the second fermentation step, which could be achieved, for example, by providing hydrogen directly as a feed to the second fermentation step or, preferably, by providing a suitable co-feed to the gasification process, such as methane or landfill gas, which would increase the hydrogen to carbon monoxide ratio in the gaseous mixture obtained from gasification.

The invention claimed is:

1. A process for the production of ethanol and butanol using at least two separate fermentation steps comprising:
    a) first fermentation step wherein a biomass feedstock is subjected to anaerobic fermentation in the presence of solventogenic bacteria comprising a mixture of bacterial strains, at a pH below 6.0 and at a temperature in the range 20 to 70 degree C. to convert the biomass feedstock to a first solution comprising acetic acid and butyric acid as the predominant products and a gasifiable feedstock residue; wherein the ratio of acetic acid to butyric acid is at least 4:1,
    b) treating said first solution predominantly comprising acetic acid and butyric acid of step (a) to produce a second solution by:
        (i) separating said first solution from said gasifiable feedstock residue; and
        (ii) separating said bacteria from said first solution; optionally pasteurizing or sterilizing said first solution;
    c) passing said gasifiable feedstock residue to a gasification step wherein it is subjected to gasification to produce a gaseous mixture comprising carbon monoxide and hydrogen, and
    d) passing said second solution from step (b) and said gaseous mixture from step (c) to one or more fermentation steps in the presence of anaerobic acetogenic bacteria comprising a mixture of bacterial strains to thereby produce ethanol and butanol.

2. A process according to claim 1, wherein the pH in the first fermentation step is maintained in the range 3 to 5.5 and the temperature in the first fermentation step is in the range 40 to 60.degree. C.

3. A process according to claim 1, wherein the first solution comprises a concentration of acetic acid in solution of 1 to 5 wt %.

4. A process according to claim 1, wherein the gasification step (c)-comprising adding methane or coal.

5. A process according to claim 1, wherein gasification step (c) comprises a co-feed comprising of landfill gas which is a mixture of predominantly methane, carbon dioxide and hydrogen sulphide obtained at a landfill site.

6. A process according claim 1 wherein said ethanol and butanol from step (d) comprises ethanol at a concentration of ethanol in solution in the range 1 to 5 wt % and butanol at a concentration of butanol in solution in the range 0.2 to 1 wt %.

7. A process according to claim 1 wherein the ethanol from step (d) is purified to 90-95 wt % ethanol by distillation followed by a drying step to give a >99 wt % ethanol.

* * * * *